United States Patent [19]

Chekroun et al.

[11] Patent Number: 4,458,086

[45] Date of Patent: Jul. 3, 1984

[54] PROCESS FOR THE PREPARATION OF 2-(THIENYL-2)- AND 2-(THIENYL-3)-ETHYLAMINES

[75] Inventors: Isaac Chekroun, Toulous; Alain Heymes; Sisteron, both of France

[73] Assignee: Sanofi, Toulouse, France

[21] Appl. No.: 393,388

[22] Filed: Jun. 29, 1982

[30] Foreign Application Priority Data

Jun. 30, 1981 [FR] France ............................. 81 13064

[51] Int. Cl.$^3$ ........................................... C07D 333/00
[52] U.S. Cl. ........................................ 549/74; 549/59; 549/60; 549/61; 549/65; 549/68; 546/284
[58] Field of Search ................. 549/74, 59, 60, 61, 549/65, 68; 546/284

[56] References Cited
PUBLICATIONS

Gilsdorf, "J. Org. Chem.", 15, 807–811 (1950).

Primary Examiner—Alan Siegel
Attorney, Agent, or Firm—Weiser & Stapler

[57] ABSTRACT

The present invention provides a process for the preparation of 2-(thienyl-2)- and 2-(thienyl-3)-ethylamines of the general formula:

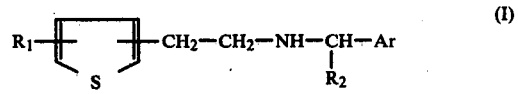

in which $R_1$, which is in the 2-, 3-, 4- or 5-position, is a hydrogen atom, a straight-chained or branched alkyl radical or a heterocyclic or non-heterocyclic aromatic radical, which is optionally mono- or polysubstituted, or $R_1$ is an alkoxy radical, a halogen atom or a nitro, carboxyl, cyano or amino group; the aminoethyl chain is in the 2- or 3-position of the thiophene nucleus; $R_2$ is a hydrogen atom or a straight-chained or branched alkyl radical or a heterocyclic or non-heterocyclic aromatic radical, which is optionally mono- or poly-substituted; and Ar is a heterocyclic or non-heterocyclic aromatic radical, which is optionally mono- or polysubstituted.

11 Claims, No Drawings

PROCESS FOR THE PREPARATION OF 2-(THIENYL-2)- AND 2-(THIENYL-3)-ETHYLAMINES

The present invention is concerned with a new process for the preparation of thienylamines.

The thienylamines with which the present invention is concerned are compounds of the general formula;

$$R_1-\text{[thiophene]}-CH_2-CH_2-NH-\underset{\underset{R_2}{|}}{CH}-Ar \quad (I)$$

in which $R_1$, which is in the 2-, 3-, 4- or 5-position, is a hydrogen atom, a straight-chained or branched alkyl radical or a heterocyclic or non-heterocyclic aromatic radical, such as a thienyl, furfuryl, pyridyl, phenyl or naphthyl radical, optinally mono- or polysubstituted by substituents such as alkyl, phenyl, halogen, nitro, cyano, amino, carboxyl or alkoxy, or $R_1$ is an alkoxy radical, a halogen atom or a nitro, carboxyl, cyano or amino group; the aminoethyl chain is in the 2- or 3-position of the thiophene nucleus, $R_2$ is a hydrogenatom or a straight-chained or branched alkyl radical or a heterocyclic or non-heterocyclic aromatic radical, such as thienyl, furyl, pyridyl, phenyl or naphthyl radical, optionally mono- or polysubstituted by substituents such as alkyl, phenyl, halogen, nitro, cyano, amino, carboxyl and alkoxy; and Ar is a heterocyclic or non-heterocyclic aromatic radical such as described above.

Some of the compounds of general formula (I) are known and are used as intermediates for the preparation of compounds used in the parmaceutical chemical industry.

Thus, by way of example, amongst the compounds which can be obtained by the new process according to the present invention, those may be mentioned which, on the one hand, may be reached in known manner (the aminoethyl radical being in the 2-position and the substituent $R_1$ being in the 4- or 5-position) to give derivatives of 4,5,6,7-tetrahydrothieno[3.2-c]pyridine and, on the other hand, (the aminoethyl radical being in the 3-position and the substituent $R_1$ being in the 4- or 5-position), to give derivatives of 4,5,6,7-tetrahydro[2,3-c]pyridine, both types of derivatives, processes for the preparation thereof and/or the therapeutic use thereof being the subject of our earlier French Pat. Nos. 73.03503; 75.03968; 75.20241; 75.23786; 75.24486; 76.00003 and 77.21517.

It is an object of the present invention to provide a simple process which is less expensive than the previously known processes for obtaining compounds of general formula (I).

Thus, according to the process of the present invention, the compounds of general formula(I) are prepared by:

(a) condensing a compound of the general formula:

$$\underset{Y}{\overset{X}{>}}\underset{\|}{\overset{O}{P}}-CH_2-NH_2 \quad (II)$$

in which X and Y, which may be the same or different, are alkyl, aryl, alkoxy, aryloxy, dialkylamino or diarylamino radicals of a type such that the organophosphorus compound of general formula (II) may be a phosphonate, a phosphinate, a phosphorus oxide or a phosphonamide, with a carbonyl compound of the general formula:

$$R_1-\text{[thiophene]}-CHO \quad (III)$$

in which $R_1$ has the same meaning as in general formula (I), to give a compound of the general formula:

$$\underset{Y}{\overset{X}{>}}\underset{\|}{\overset{O}{P}}-CH_2-N=C(H)-\text{[thiophene]}-R_1 \quad (IV)$$

in which $R_1$, X and Y have the same meanings as above;

(b) treating the compound of general formula (IV) with a base of the general formula $B^\ominus M^\oplus$ to give a carbanion of the general formula:

$$\underset{Y}{\overset{X}{>}}\underset{\|}{\overset{O}{P}}-\underset{\underset{}{}}{\overset{M^\oplus}{CH^\ominus}}-N=C(H)-\text{[thiophene]}-R_1 \quad (V)$$

in which $R_1$, X and Y have the same meanings as above;

(c) converting the carbanion (V) by the action of heat into a compound of the general formula:

$$\underset{Y}{\overset{X}{>}}\underset{\|}{\overset{O}{P}}-\overset{M^\oplus}{N^\ominus}-CH=CH-\text{[thiophene]}-R_1 \quad (VI)$$

in which $R_1$, X and Y have the same meanings as above, which, after taking up in water, gives a compound of the general formula:

$$\underset{Y}{\overset{X}{>}}\underset{\|}{\overset{O}{P}}-\overset{H}{N}-CH=CH-\text{[thiophene]}-R_1 \quad (VII)$$

in which $R_1$, X and Y have the same meanings as above, this reaction generally being carried out at a temperature of from $-78°$ to $+150°$ C., chosen specifically as a function of the base $B^\ominus M^\oplus$ and at the upper part of the range especially for carrying out stage (c);

(d) the compound of general formula (VII) is converted by a reducing agent into a compound of the general formula:

$$\underset{Y}{\overset{X}{>}}\underset{\|}{\overset{O}{P}}-\overset{H}{N}-CH_2-CH_2-\text{[thiophene]}-R_1 \quad (VIII)$$

in which $R_1$, X and Y have the same meanings as above;

(e) successively reacting the compound (VIII) first with a base of the general formula $B'^\ominus M'^\oplus$ and then with a halogen derivative of the general formula:

$$Ar-CHX-R_2 \quad (IX)$$

in which Ar and R₂ have the same meanings as above and X is a halogen atom, to give a compound of the general formula:

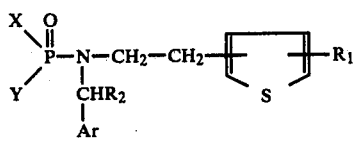  (X)

in which R₁, R₂, X and Y have the same meanings as above;

(f) and finally converting the compound of general formula (X) by the action of an acid into a compound of general formula (I).

The process according to the present invention may be illustrated by the following reaction scheme:

Stage (a)

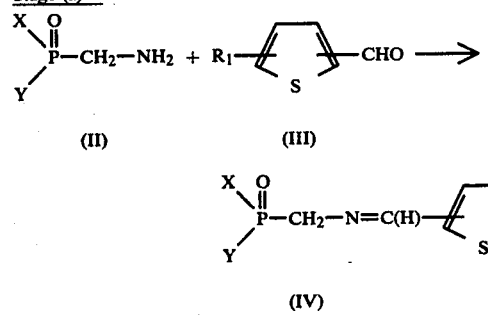

Stage (b)

Stage (c)

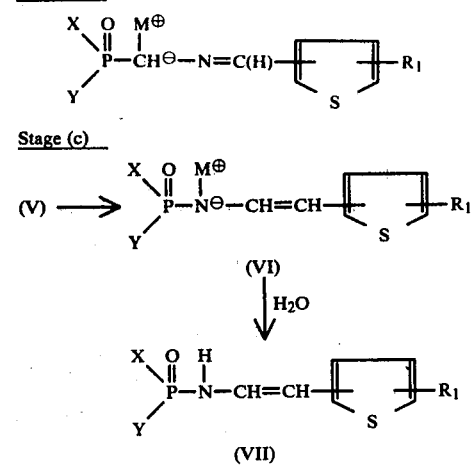

Stage (d)

(VII) $\xrightarrow{\text{(reduction)}}$

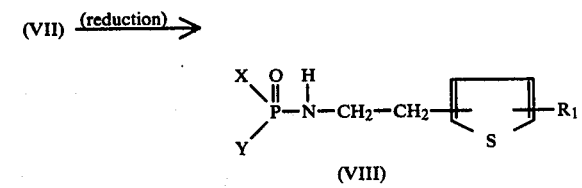

Stage (e)

(VIII) $\xrightarrow[\text{(2°) AR—CHX—R}_2]{\text{(1°) B'}^-\text{M'}^+}$

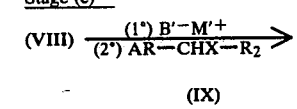

(IX)

-continued

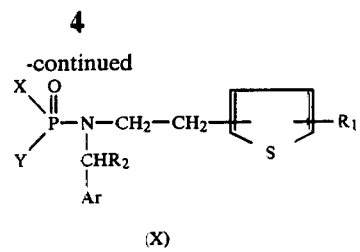

(X)

Stage (f)

(X) $\xrightarrow{H^\oplus}$ R₁—⟨S⟩—CH₂—CH₂—NH—CH—Ar
                                                    |
                                                    R₂

(I)

According to a variant of the process of the present invention, the order of stages (d) and (e) can be reversed in the following manner:

Stage (d) (bis)

(VII) $\xrightarrow[\text{(2°) Ar—CHX—R}_2]{\text{(1°) B'}^-\text{M'}^+}$

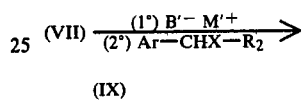

(VII bis)

Stage (e) (bis)

(VII bis) $\xrightarrow{\text{reduction}}$

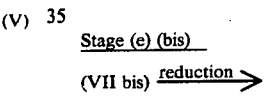

(X)

The process may advantageously be carried out in the following manner:

(a) the organophosphorus compounds of general formula (II), which are easily obtainable by well-known methods of preparation, such as are described, for example, by I.C. Popoff et al. (J. Org. Chem. 28, 2898/1963), may be reacted with the carbonyl derivatives of general formula (III) in the absence of solvent and catalyst, water formed in the course of the reaction being eliminated at the end of the operation by appropriate means. The condensation may be advantageously carried out in a solvent, such as an aromatic hydrocarbon, for example toluene, or an alcohol, for example ethanol, in which it is possible to eliminate the water by azeotropic distillation. The condensation may also be carried out advantageously, for the purpose of speed, in the presence of a catalytic amount of a mineral acid or of an organic acid, for example p-toluenesulphonic acid. The temperature at which the condensation is carried out is variable but is generally from 20° to 120° C.

(b,c) The base B⊖M⊕ used in this stage may be an alkali metal hydride, especially sodium, lithium or potassium hydride, an amide or alkylamide and especially a dialkylamide of an alkali metal, such as lithium diisopropylamide, or an organometallic compound, especially an organolithium compound, such as n-butyl lithium, or an organosodium or organomagnesium compound. It is also possible to use alcoholates of alkali metals and alkaline earth metals, such as sodium methylate, lithium methylate, potassium methylate, magnesium methylate, potassium tert.-butylate or sodium tert.-amylate. It is also possible to use an alkali metal or alkaline earth metal hydroxide, such as sodium, lithium, potassium or magnesium hydroxide.

In general, use is made of a stoichiometrically equivalent amount of the base B⊖M⊕ or a slight excess thereof, for example, 10% referred to the stoichiometrically equivalent amount. However, it is also possible to use the base in an amount which is distinctly lower than the stoichiometrically equivalent amount.

It is here convenient to mention the operational variant in which the order of stages (d) and (e) is reversed, using a stoichiometric equivalent of the base B⊖M⊕, which may be advantageous for avoiding the isolation of the compound of general formula (VII) and directly reacting (VII) with the halogenated derivative of general formula (IX) to avoid also having to use the base B'⊖M'⊕.

Generally, the reaction is carried out at a temperature of from −78° to +150° C., the temperature chosen being a function of the base B⊖M⊕ and at the upper part of the range, especially for carrying out stage (c).

The preferred solvents used include linear and cyclic ethers, such as tetrahydrofuran, hydrocarbons, especially aromatic hydrocarbons, such as benzene, toluene and xylenes, alcohols, amides, especially dimethylformamide, and sulphoxides, especially dimethyl sulphoxide. It may also be advantageous, especially when using a metal hydroxide, to work in a two-phase system (water+solvent, which solvent may be a halogenated one, such as dichloromethane, or an aromatic hydrocarbon, such as benzene, toluene or xylenes, in the presence of a phase transfer catalyst, especially a quaternary ammonium compound, such as tetra-n-butyl-ammonium iodide, or a phosphonium salt. Conventional methods can be used for isolating the compound (VII).

(d) The reduction of the compounds of general formula (VII) is advantageously carried out by means of a mixed alkali metal hydride, especially a borohydride, such as sodium or potassium borohydride. The reduction is carried out in an inert solvent medium, such as an ether, for example tetrahydrofuran or dioxan, or also in an alcohol, such as methanol or ethanol.

The reduction can also be carried out by means of a catalytic hydrogenation in homogeneous or heterogeneous phase under known conditions.

(e) The base B'⊖M'⊕ used in the first part of the fifth stage may be chosen from those mentioned above for use in stages (b) and (c). In general, it is used in a stoichiometrically equivalent amount but may be used in a slightly greater amount than this of, for example, 5 to 10% more than this equivalent amount.

The operation is generally carried out at a temperature of from −20° to +100° C. with a preference for the lower range. The solvents used may be the same as those mentioned above in stage (b).

In the second part of this stage, the halogen compound of general formula (IX) is reacted with the reaction mixture as defined above at a temperature which is generally similar to that used in the first part.

(f) The acid catalysed splitting of the phosphorus-nitrogen bond in a compound (IX) may be carried out by means of a mineral acid, such as hydrochloric acid or hydrobromic acid, but also with an organic acid and especially a strong acid, such as a sulphonic acid, for example benzenesulphonic acid or p-toluenesulphonic acid. The solvents preferably used are ethers and especially cyclic ethers, such as tetrahydrofuran or dioxan, alcohols, such as methanol or ethanol, amides, especially dimethylformamide, and sulphoxides, especially dimethyl sulphoxide. It is possible to operate in these solvents in the absence of water but also in mixtures containing a variable amount of water. Finally, it is also possible to operate entirely in an aqueous medium.

In general, two stoichiometric equivalents of acid are used.

Generally speaking, the operation is carried out at a temperature of from 0° to 100° C. and especially of from 30° to 70° C.

The compounds of general formula (I) thus obtained may be subsequently isolated and purified by conventional methods. In order to carry out these operations, it may be advantageous to convert the free bases of general formula (I) into their salts, for example their acid-addition salts with mineral or organic acids. The free bases (I) can subsequently be liberated from these salts in known manner.

The present invention is also concerned with the intermediates obtained at the various stages of the synthesis:

Compounds of the general formula:

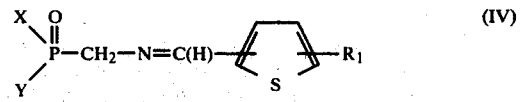
(IV)

Compounds of the general formula:

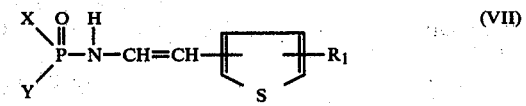
(VII)

Compounds of the general formula:

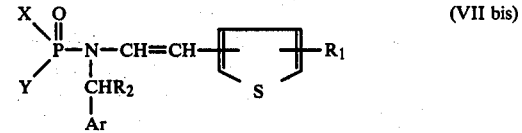
(VII bis)

Compounds of the general formula:

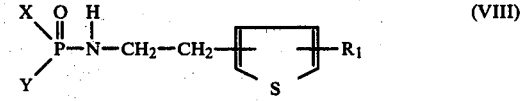
(VIII)

Compounds of the general formula:

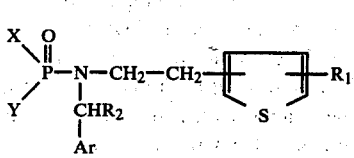

Compounds of the general formula:

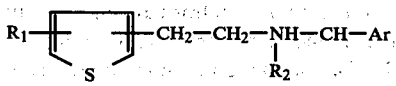

The following Examples are given for the purpose of illustrating the present invention:

EXAMPLE 1

Preparation of N-o-chlorobenzyl-2-(thienyl-2)-ethylamine hydrochloride

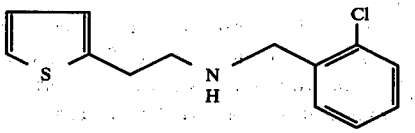

Variant A

Stage (a)

Diethyl N-(thienylidene-2)-aminomethylphosphonate

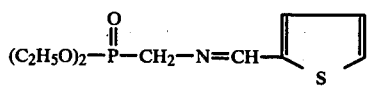

11.2 g. (0.1 mole) then-2-aldehyde are added to 16.7 g. (0.1 mole) diethyl aminomethylphosphonate in 200 ml. ethanol and the reaction mixture then heated under reflux for 30 minutes, the water formed in the course of the reaction being eliminated by azeotropic distillation. After complete evaporation of the solvent, there are obtained 28 g. (about 100% of theory) of the desired pure compound in the form of a yellow oil (CPL, CCM and CPG).

IR (film): C=N, 1645 cm$^{-1}$; P=O, 1260 cm$^{-1}$; P—O—C, 1060–1080 cm$^{-1}$.

NMR (CDCl$_3$) δ/TMS: 1.3 ppm, (t, 6H); 3.9 to 4.45 ppm, (m, 6H); 7 to 7.6 ppm, (m, 3H); 8.5 ppm, (d, 1H).

Stages (b) and (c)

Diethyl β-(thienyl-2)-N-vinylphosphoramidate

A solution of 27.9 g. (0.1 mole) diethyl N-(thienylidene-2)-aminomethylphosphonate in 40 ml. tetrahydrofuran is added dropwise to a suspension of 11.2 g. (0.1 mole) potassium tert.-butylate in 160 ml. tetrahydrofuran. In the course of the addition, the temperature increases from 20° C. to 35° C. At the end of the addition, the temperature is maintained at 40°-45° C. for 30 minutes, whereafter the reaction mixture is introduced into 400 ml. of a saturated aqueous solution of ammonium chloride. The aqueous phase is extracted with diisopropyl ether and the ethereal extracts are combined and washed with a saturated aqueous solution of sodium chloride, dried with anhydrous sodium sulphate and then evaporated to give 20.9 g. (75% of theory) of the desired product in the form of a yellow oil.

NMR (CDCl$_3$) δ/TMS 1.3 ppm, (t, 6H); 3.95 ppm, (ddeq, 4H); 6.35 ppm, (m, 1H); 6.9 to 7.5 ppm, (m, 5H) after exchange with D$_2$O (m, 4H).

IR (film): NH, 3300 cm$^{-1}$; C=C, 1650 cm$^{-1}$; P—O, 1250 cm$^{-1}$; P—O—C, 1050 cm$^{-1}$.

Stage (d)

Diethyl N-[2-(thienyl-2)-ethyl]-phosphoramidate 20.9 g. (0.075 mole) of the diethyl β-(thienyl-2)-N-vinylphosphoramidate obtained above are added to a solution of 2.85 g. (0.075 mole) of sodium borohydride in 200 ml. ethanol. During the addition, the temperature rises and then stabilises at 30° C. After a further 2 hours stirring, the temperature of the reaction mixture is increased to 45° to 50° C. for 1 hour, then the ethanol is evaporated off and the residue is taken up in a mixture of diisopropyl ether and water. The aqueous phase is re-extracted several times with diisopropyl ether and the combined organic phases are washed with water, dried with anhydrous sodium sulphate and evaporated to give 21 g. (about 75% of theory, referred to the aminomethylphosphonate used as starting material) of the desired product in the form of a yellow oil.

IR (film): 3400 cm$^{-1}$; 1520 cm$^{-1}$; 1275 cm$^{-1}$; 1210 cm$^{-1}$.

NMR (CDCl$_3$) δ/TMS: 1.3 ppm, (t, 6H); 3.1 ppm, (m, 5H) Ar—CH$_2$—CH$_2$—NH— (by exchange with D$_2$O there is obtained 3.1 ppm (m, 4H); 4.05 ppm, (ddeq, 4H); 6.75 to 7.2 ppm, (m, 3H).

Stage (e)

Diethyl N-o-chlorobenzyl-N-[2-(thienyl-2)-ethyl]-phosphoramidate

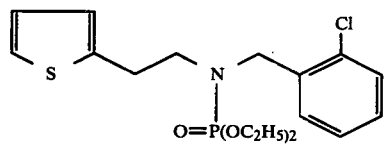

21 g. (0.075 mole) Diethyl N-[2-(thienyl-2)-ethyl]-phosphoramidate in 20 ml. toluene are added dropwise at ambient temperature, while stirring, to a suspension of 3.6 g. (0.075 mole) sodium hydride (50% in oil) in 150 ml. toluene. The reaction mixture becomes red and is kept for 1 hour at 80° C. and then 16.1 g. (0.1 mole) o-chlorobenzyl chloride are added dropwise. The reaction mixture is stirred for 3 hours at 80° C. and then, after cooling, washed with water. The toluene phase is subsequently evaporated to give the desired phosphoramidate (contaminated with excess o-chlorobenzyl chloride) in the form of an oil which is used in the following stage. A pure sample may be obtained by chromatography on a silica column (eluant: ethyl acetate).

IR (film): 3000 cm$^{-1}$; 1550 cm$^{-1}$; 1250 cm$^{-1}$; 1050 cm$^{-1}$.

NMR (CDCL$_3$) δ/TMS: 1.3 ppm, (t, 6H); 3.1 ppm, (m, 4H); 4 ppm, (ddeq, 4H); 4.45 ppm, (d, 2H); 6.8 to 7.6 ppm, (m, 7H).

Stage (f)

N-o-Chlorobenzyl-2-(thienyl-2)-ethylamine hydrochloride

The crude phosphoramidate obtained above is treated with 200 ml. of a 3N aqueous solution of hydrochloric acid for 2 hours at 90° C. After extraction at this temperature with two 20 ml. amounts of 1,2-dichloroethane and cooling the aqueous solution, a precipitate is formed which is filtered off. After drying, there are thus obtained 15 g. (52% of theory, referred to the ethyl aminomethylphosphonate) of the desired hydrochloride in the form of white crystals; m.p. 143° C.

IR (KBr tablets): 3400 cm$^{-1}$; 2900 to 2600 cm$^{-1}$; 1575 cm$^{-1}$; 1450 cm$^{-1}$.

NMR (DMSO d$_6$) δ/TMS: 7 to 7.8 ppm, (m, 8H); 3.35 ppm, (s, 4H); 4.15 ppm, (s, 2H); about 10 ppm, (m, 2H), exchangeable with D$_2$O.

Analysis: C$_{13}$H$_{14}$ClNS, HCl (M.W. 288.236): calc.: C,54.16%; H,5.24%; N,4.85%; found: C,54.11%; H,5.28%; N,4.80%.

EXAMPLE 2

Preparation of N-o-chlorobenzyl-2-(2-thienyl-2)-ethylamine hydrochloride

Variant B

Stage (a)

Diethyl N-(thienylidene-2)-aminomethylphosphonate 0.1 Mole of the desired product is prepared in the manner described in Example 1.

Stages b, d bis

Ethyl N-o-chlorobenzyl-β-(thienyl-2)-N-thienylphosphoramidate

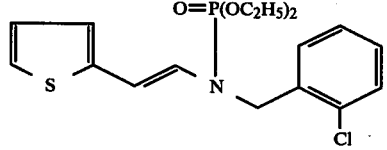

A solution of 27.9 g. (0.1 mole) diethyl N-(thienylidene-2)-aminomethylphosphonate in 40 ml. tetrahydrofuran is added dropwise to a suspension of 11.2 g. (0.1 mole) potassium tert.-butylate in 160 ml. tetrahydrofuran. In the course of the addition, the temperature increases from 20° C. to 35° C. At the end of the addition, the temperature is increased to 40° to 45° C. for 30 minutes, then 16.1 g. (0.1 mole) o-chlorobenzyl chloride are added dropwise. When the addition is finished, the reaction mixture is refluxed for 3 hours and then the tetrahydrofuran is evaporated off. The residue is taken up in diisopropyl ether and the ethereal phase is washed with water, dried and then evaporated to give 32.7 g. (85% of theory) of the desired product in the form of a yellow-orange oil which is used as such for the next stage. A sample purified by chromatography on a silica column (eluent: ethyl acetate) has the following characteristics:

IR (film): 3000 cm$^{-1}$; 1650 cm$^{-1}$; 1240 cm$^{-1}$; 1045cm$^{-1}$.

NMR (CDCl$_3$) δ/TMS: 1.3 ppm, (t, 6H); 4.05 ppm, (m, 6H); 6.7 to 7.5 ppm, (m, 7H).

Stage (e bis)

Diethyl N-o-chlorobenzyl-N-[2-(thienyl-2)-ethyl]-phosphoramidate

The crude product obtained in the previous stage is added to a suspension of 6.5 g. (0.17 mole) sodium borohydride in 100 ml. dioxan. The reaction mixture is cooled to 0° C. and 14.3 g. (0.17 mole) trifluoroacetic acid are then added dropwise thereto. When the addition is finished, the reaction mixture is boiled under reflux for 1 hour, then, after cooling, hydrolysed by adding 200 ml. water. The reaction mixture is extracted with methylene chloride and the organic phase is isolated, dried with anhydrous sodium sulphate and evaporated. There are obtained 33 g. (85% of theory, referred to the aminomethylphosphonate used as starting material) of the desired phosphoramidate in the form of a yellow oil. A sample purified by chromatography on a silica column has the same characteristics as the product obtained in variant A above.

Stage (f)

N-o-Chlorobenzyl-2-(thienyl-2)-ethylamine hydrochloride

Operating in the manner described in Example 1, there are obtained 17.3 g. (yield 60% of theory, referred to the diethyl aminomethylphosphonate) of N-o-chlorobenzyl-2-(thienyl-2)-ethylamine which has physical, spectral and analytical characteristics identical with those of the product obtained in Example 1.

We claim:

1. Process for the preparation of 2-(thienyl-2)- and 2-(thienyl-3)-ethylamines of the general formula:

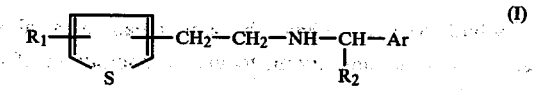

in which R$_1$, which is in the 2-, 3-, 4- or 5-position, is a hydrogen atom, a straight-chained or branched alkyl radical or a heterocyclic or non-heterocyclic aromatic radical, which is optionally mono- or polysubstituted, or R$_1$ is an alkoxy radical, a halogen atom or a nitro, carboxyl, cyano or amino group; the aminoethyl chain is in the 2- or 3-position of the tiophene nucleus; R$_2$ is a hydrogen atom or a straight-chained or branched alkyl radical or a heterocyclic or non-heterocyclic aromatic radical, which is optionally mono- or polysubstituted; and Ar is a heterocyclic or non-heterocyclic aromatic radical, which is optionally mono- or polysubstituted, which comprises the steps of heating a carbanion of the general formula:

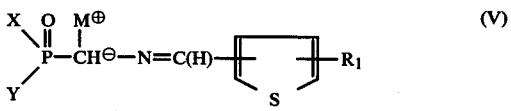

in which M+ is an alkali or alkaline earth metal, X and Y, which may be the same or different, are alkyl, aryl, alkoxy, aryloxy, dialkylamino or diarylamino radicals and R$_1$ has the same meaning as above, so as to form a compound of the general formula:

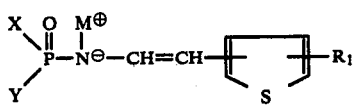

(VI)

in which $M^+R_1$, X and Y have the same meanings as above, treating with water so as to yield, a compound of the general formula:

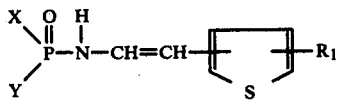

(VII)

in which $R_1$, X and Y have the same meanings as above, reduction of which gives a compound of the general formula:

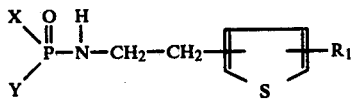

(VIII)

in which $R_1$, X and Y have the same meanings as above, reacting the compound formed with a base of the general formula $B'^-M'^+$ wherein $B'^-$ is hydrogen, amide, dialkylamide, alkyl, alkylate or hydroxy, $M'^+$ is an alkali or alkaline earth metal, and reacting with a halogen derivative of the general formula:

$$Ar-CHX-R_2 \quad (IX)$$

in which Ar and $R_2$ have the same meanings as above and X is a halogen atom, to give a compound of the general formula:

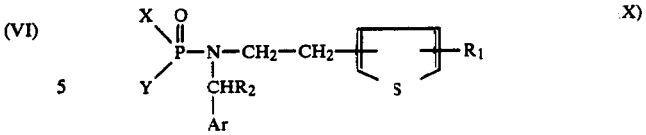

(X)

in which Ar, $R_1$, $R_2$, X and Y have the same meanings as above, which is finally converted into a compound of general formula (I) by the action of an acid.

2. The process according to claim 1, which comprises using a stoichiometric amount of the base $B'^-M'^+$, the compound of the formula (VII) is reacted with the halogen derivative of the formula (IX) and then reduced to give the compound of the formula (X) directly.

3. Process according to claim 1 or 2, wherein the conversion of the compound of formula (V) into compound of formula (VI) is carried out at a temperature of from $-78°$ C. to $+150°$ C.

4. Process according to claim 3, wherein the temperature is selected as a function of the base in the upper part of the range.

5. Process according to any one of claims 1, 2, 3 or 4 wherein the reaction is carried out in an organic solvent.

6. Process according to claim 5, wherein the solvent is a straight-chained or cyclic ether, an aromatic hydrocarbon, an alcohol, an amide or a sulphoxide.

7. Process according to any of claims 1, 2, 3, 4, 5 or 6 wherein the reduction is carried out with an alkali metal borohydride.

8. Process according to claim 7, wherein the borohydride is sodium or potassium borohydride.

9. Process according to claim 1 wherein 2-(thienyl-3)-ethylamines, are prepared.

10. The process according to claim 1 wherein 2-(thienyl-2)-ethylamines are prepared.

11. The process according to claim 1 wherein N-o-chlorobenzyl-2-(thienyl-2)-ethylamine hydrochloride is prepared.

* * * * *